(12) United States Patent
Monif

(10) Patent No.: US 9,895,069 B2
(45) Date of Patent: Feb. 20, 2018

(54) SYSTEMS AND METHODS TO MEASURE FLUID IN A BODY SEGMENT

(71) Applicant: King Saud University, Riyadh (SA)

(72) Inventor: Mamdouh Monif Monif, Riyadh (SA)

(73) Assignee: King Saud University, Riyadh (SA)

( * ) Notice: Subject to any disclaimer, the term of this patent is extended or adjusted under 35 U.S.C. 154(b) by 258 days.

(21) Appl. No.: 14/287,974

(22) Filed: May 27, 2014

(65) Prior Publication Data

US 2015/0088018 A1    Mar. 26, 2015

Related U.S. Application Data

(63) Continuation of application No. PCT/US2011/062486, filed on Nov. 29, 2011.

(51) Int. Cl.
*A61B 5/02* (2006.01)
*A61B 5/0295* (2006.01)
*A61B 5/0456* (2006.01)
*A61B 5/0205* (2006.01)
*A61B 5/0245* (2006.01)
*A61B 5/053* (2006.01)
*A61B 5/00* (2006.01)

(52) U.S. Cl.
CPC .......... *A61B 5/0295* (2013.01); *A61B 5/0205* (2013.01); *A61B 5/0245* (2013.01); *A61B 5/0456* (2013.01); *A61B 5/053* (2013.01); *A61B 5/0535* (2013.01); *A61B 5/6814* (2013.01); *A61B 5/6822* (2013.01); *A61B 5/7278* (2013.01); *A61B 5/742* (2013.01)

(58) Field of Classification Search
CPC ... A61B 5/0537; A61B 5/6833; A61B 5/0295; A61B 5/0456
See application file for complete search history.

(56) References Cited

U.S. PATENT DOCUMENTS

| 4,008,712 A * | 2/1977 | Nyboer ................ A61B 5/0537 600/547 |
| 6,511,438 B2 | 1/2003 | Bernstein et al. |
| 2008/0275352 A1 | 11/2008 | Shapira et al. |
| 2009/0259132 A1 | 10/2009 | Bernstein |
| 2011/0196245 A1 * | 8/2011 | Poupko .............. A61B 5/02028 600/506 |

OTHER PUBLICATIONS

International Search Report dated Jun. 22, 2012 for International Appl. No. PCT/US2011/062486, 3 pp.

* cited by examiner

*Primary Examiner* — Michael D Abreu
(74) *Attorney, Agent, or Firm* — Hauptman Ham LLP

(57) ABSTRACT

The present disclosure introduces systems and methods to measure fluid in a body segment. In one embodiment, a computer system used to measure fluid in a body segment is described. A current generation module may be used to emit an electrical through at least one body segment. The electrical current may be used to measure fluid-volume content of the at least one body segment. An electrode module having a plurality of electrodes may be attached to the current generation module. A signal-processing module may be used to measure changes in the electrical current through at least one body segment. Further, an impedance module may be used to calculate fluid-volume change in at least one body segment and determine the flow of fluid through the at least one body segment. Other embodiments also are described.

2 Claims, 6 Drawing Sheets

SYSTEMS AND METHODS TO MEASURE FLUID IN A BODY SEGMENT

BACKGROUND

Impedance plethysmography is a medical test, which measures small changes in electrical resistance throughout body segments. Such measurements can be useful in determining fluid volume changes in a body segment. Measuring fluid flow through a body segment may be useful in helping medical professionals determine the presence of existing or potential health issues in a patient. Importantly, impedance plethysmography accomplishes this task in a manner that is not invasive to a patient.

SUMMARY

The present disclosure introduces systems and methods to measure fluid in a body segment. In one embodiment, a computer system used to measure fluid in a body segment is described. A current generation module may be used to emit an electrical through at least one body segment. The electrical current may be used to measure fluid-volume content of the at least one body segment. An electrode module having a plurality of electrodes may be attached to the current generation module. A signal-processing module may be used to measure changes in the electrical current through at least one body segment. Further, an impedance module may be used to calculate fluid-volume change in at least one body segment and determine the flow of fluid through the at least one body segment. Other embodiments are also described.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The detailed description is set forth with reference to the accompanying figures, in which the left-most digit of a reference number identifies the figure in which the reference number first appears. The use of the same reference numbers in different figures indicates similar or identical items or features.

DETAILED DESCRIPTION

The following detailed description is divided into several sections. A first section presents a system overview. A next section provides methods of using example embodiments. The following section describes example implementations. The next section describes the hardware and the operating environment in conjunction with which embodiments may be practiced. The final section presents the claims.

System Level Overview

Figure 1:
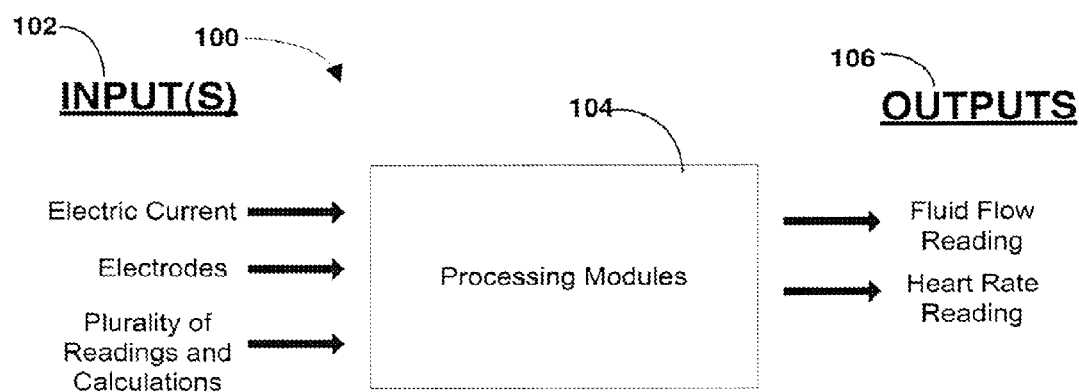
FIG. 1 is a block diagram illustrating a general overview of a fluid measurement system, according to an example embodiment.

FIG. 1 comprises a block diagram illustrating a general overview of a fluid measurement system according to an example embodiment 100. Generally, the fluid measurement system 100 may be used to measure the flow of fluid through a body segment. The fluid measurement system 100 is designed to measure blood flow to a body segment in a continuous and non-invasive manner. For example, system 100 can be used to measure the volume of blood in the carotid artery noninvasively using bioimpedance in association with the timing of the heartbeat to calculate the volume of blood that is fed to the brain. In this exemplary implementation, the fluid measurement system 100 comprises inputs 102, computer program processing modules 104, and outputs 106.

Figure 6:
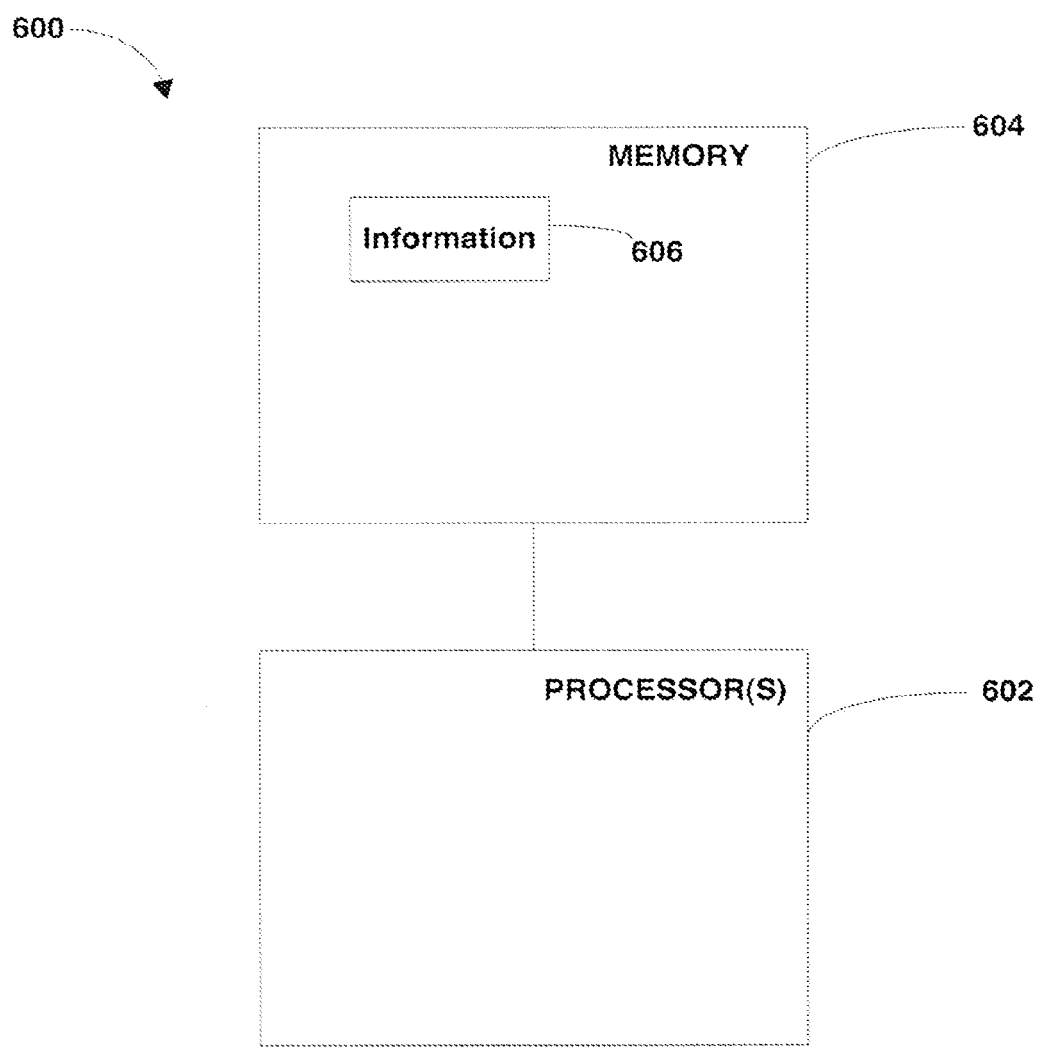
FIG. 6 is a block diagram illustrating a fluid measurement system, according to an example embodiment.

In one embodiment, the fluid measurement system 100 may be a computer system such as shown in FIG. 6. Inputs 102 are received by processing modules 104 and processed into outputs 106. Inputs 102 may include an electric current, a plurality of electrodes, and a plurality of readings and calculations.

A first input 102 is an electric current, which may be generated and applied through at least one body segment of a patient. A patient may be any living being, including humans and animals. The electric current may be produced by an electrical source. An electrical source may be any device or apparatus capable of generating an electric current. One example of an electric source may be a current generator circuit. In order to measure the fluid in a body segment continuously, the electric current should be constant. The electric current may be a constant sinusoidal alternating current.

A second input 102 may be a plurality of electrodes. The electric current may run through a plurality of electrodes connected to a body segment. In one embodiment, some of the plurality of electrodes may also be directly connected to the electrical energy source. In an alternative embodiment, each of the plurality of electrodes may be connected to the electrical source. Electrical impedance of the plurality of electrodes may be measured by applying a constant current through the body segment. Changes in flow of an electrical current through a body segment may occur because of changes in fluid-volume content of the body segment. In an exemplary embodiment, the fluid of a body segment may be blood. Blood is a conductive electrolyte, and the electrical impedance of a given body segment is dependent on the amount of blood within the segment. As blood enters the body segment, during each cardiac cycle or as a result of fluid redistribution, its impedance decreases. This change in electrical impedance may be measured by the plurality of electrodes.

A third input 102 may be a plurality of readings and calculations. The plurality of readings may be electrical impedance readings including both original impedance readings and changes in fluid-volume content of a body segment. The plurality of calculations may include applying mathematical equations such as a Nyboer formula to the electrical impedance readings to determine patient vital signs. Patient vital signs may physiological statistic taken to assess basic bodily functions. Some common patient vital signs may include blood flow to a particular body segment and also heart rate. Please refer to the "example implementations" section of this detailed description for additional reference to the Nyboer formula.

Processing modules 104 generally include routines, computer programs, objects, components, data structures, etc., that perform particular functions or implement particular abstract data types. The processing modules 104 receive inputs 102 and apply the inputs 102 to capture and process data producing outputs 106. The processing modules 104 are described in more detail by reference to FIG. 2.

Outputs 106 are produced by receiving the inputs 102 and applying processing modules 104 to the inputs 102. The outputs 106 may include a fluid flow reading and a heart rate reading. The fluid flow reading may be determined by using the plurality of calculations to calculate the fluid-volume change occurring in a body segment and multiplying that value by the heart rate reading. A heart rate reading can be determined from the electrical impedance readings. These outputs 106 may provide an indication of a patient's health status.

Figure 2:
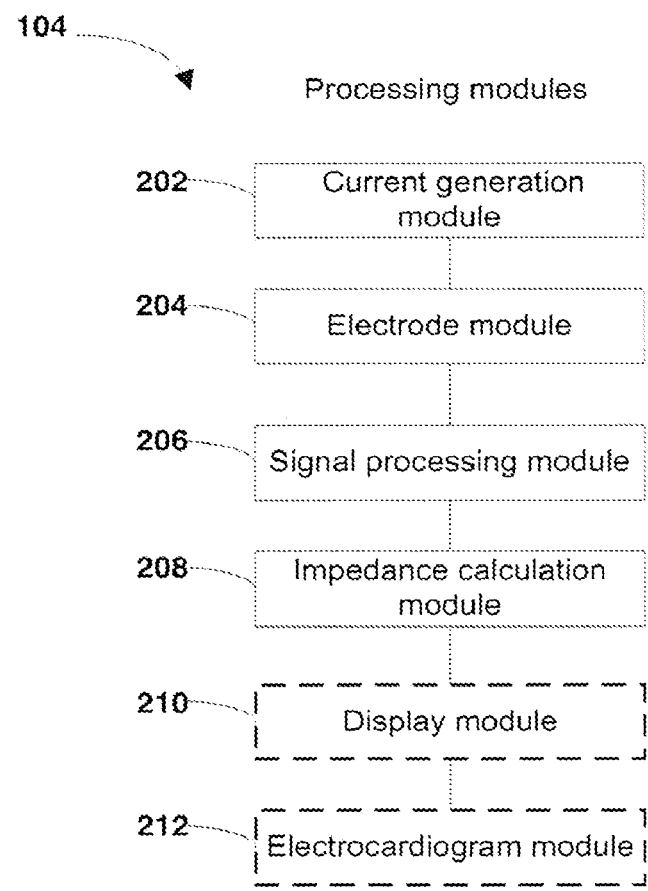
FIG. 2 is a block diagram illustrating a set of computer program modules to enable fluid measurement of a body segment into a computer system, according to an example embodiment.

FIG. 2 is a block diagram of the processing modules 104 of the system shown in FIG. 1, according to various embodiments. Processing modules 104, for example, comprise a current generation module 202, an electrode module 204, a signal-processing module 206, and an impedance calculation module 208. Alternative embodiments are also described below.

The first module, a current generation module 202, may be used to generate an electric current. The generated electric current may be emitted through at least one body segment. The emitted electric current may be used to measure a fluid-volume content of the at least one body segment over a period of time. In one embodiment, the current generated by the current generation module 202 may be continuous. Providing a continuous and constant current through a body segment may allow accurate capturing of changes in the fluid-volume content of the body segment. The current generation module may be connected to an electrical source to generate an electrical current. In an exemplary embodiment, a current generator circuit may be used to produce a constant sinusoidal alternating current, which can be applied through a body segment.

The second module, an electrode module 204, may have a plurality of electrodes connected to the current generation module 202 to conduct the electrical current. A plurality of electrodes may be attached to at least one body segment of a patient. In one embodiment, the plurality of electrodes may be attached to multiple body segments of a patient, to measure fluid flow more accurately throughout the body of a patient. Any type of electrode may be used including bare or shielded electrodes comprised of mild steel, high-carbon steel, special alloy steel, cast iron, or nonferrous materials, among others.

The third module, a signal-processing module 206, may be used to measure changes in flow of the electrical current through at least one body segment. Changes in the electrical current may occur as the fluid-volume of a body segment changes. In one embodiment, the signal-processing module 206 may use a four (4)-electrode method to determine impedance changes of the electrical current through a body segment. A constant sinusoidal alternating current may be applied by the circuit generation module 202, which may pass longitudinally through a first set of electrodes (part of the electrode module 204). Next, a voltage drop is measured between a second set of electrodes (part of electrode module 204). The change in voltage of the constant sinusoidal alternating current may be used by the impedance calculation module 208 to calculate a fluid-volume content change in a body segment.

A fourth module, an impedance calculation module 208 may be used to calculate a fluid flow through a body segment. Determining a fluid-volume change in the body segment and applying a Nyboer formula calculation may do this. Changes in the electrical impedance of a body segment may occur as the fluid-volume content changes. Changes in electrical impedance readings may be recorded and as the fluid-volume content changes. In one embodiment, the fluid of a body segment may be blood. As blood enters a body segment, during each cardiac cycle or as a result of fluid redistribution, its impedance decreases. The fluid-volume content change may be determined and used in a calculation to determine fluid flow in a body segment by applying a Nyboer formula. Please refer to the "example implementations" section of this detailed description for a breakdown of the Nyboer formula.

In an alternative embodiment, an additional processing module 104, namely, a display module 210 may be used to illustrate a representation of the electrical current through the at least one body segment. The display module 210 may be used to represent electrical impedance readings and calculations. The display module 210, to visually project impedance readings and calculations, may use a monitor or screen display. In one example embodiment, the display module 210 may illustrate numerical values of patient vital signs. In another embodiment, the display module 210 may illustrate more complex graphical and pictorial representations of patient vital signs.

Yet another alternative embodiment, an additional processing module 104, namely, an electrocardiogram ("ECG") module 212 may be used to synchronize signal processing and calculation of a heart rate. The ECG module 212 may produce an ECG signal, which can measure the activity of a heart over a period of time. The ECG module 212 may detect the R-wave-to-R-wave interval ("RR interval"), which may be used to measure electric stimulus as it passes through the heart. The RR interval may be used to determine a heart rate reading. A heart rate reading can be used in the calculation to determine flow of fluid through a body segment.

Exemplary Methods

In this section, particular methods to measure fluid in a body segment and example embodiments are described by reference to flow charts. The methods to be performed may constitute computer programs made up of computer-executable instructions.

Figure 3:
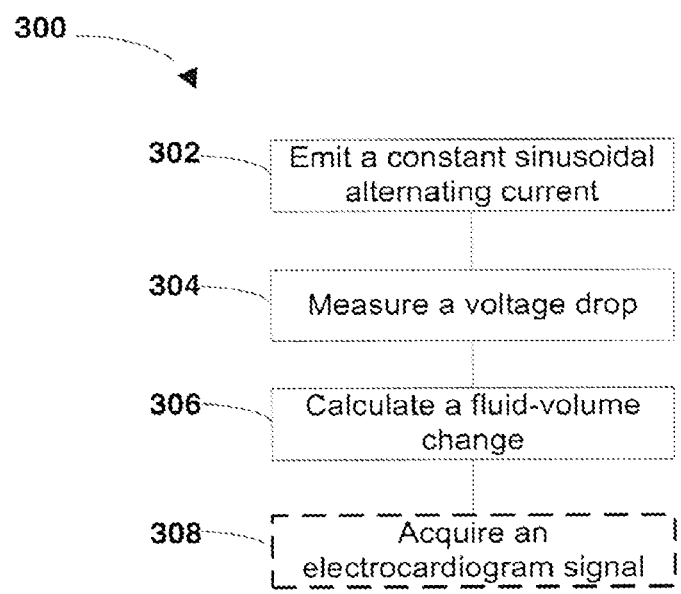
FIG. 3 is a block diagram illustrating a method to measure fluid in a body segment, according to one embodiment.

FIG. 3 is a block diagram illustrating a method to measure fluid in a body segment, according to an example embodiment. The method 300 represents one embodiment of a fluid measurement system such as the fluid measurement system 100 described in FIGS. 1 and 6, respectively. The method 300 may be implemented by emitting a constant sinusoidal alternating current through a first set of electrodes attached to at least one body segment (block 302), measuring a voltage drop between a second set of electrodes attached to the at least one body segment (block 304), and calculating a fluid-volume change in the at least one body segment (block 306).

A constant sinusoidal alternating current is emitted through a first set of electrodes at block 302. The constant sinusoidal alternating current of block 302 may be a constant current of one (1) milliampere ("mA") and one hundred (100) kilohertz ("kHz"). In an exemplary embodiment, the constant sinusoidal alternating current of block 302 may pass longitudinally through the first set of electrodes. The first set of electrodes of block 302 may be attached to at least one body segment. In one embodiment, the first set of electrodes may be attached to multiple body segments. An electrical source may be used to generate the constant sinusoidal alternating current of block 302. One example of an electric source used to produce an electrical current may be a current generator circuit.

At block 304, a voltage drop is measured between a second set of electrodes attached to the at least one body segment. Voltage drop between electrodes may be measured using a voltmeter or calculated using Ohms law. Calculating a voltage drop between electrodes may be useful in determining the fluid-volume content change of a body segment.

A fluid volume change in the at least one body segment is calculated at block 306. The fluid-volume change in the at least one body segment may be calculated by applying a Nyboer formula. Please refer to the "example implementations" section of this detailed description for a breakdown of the Nyboer formula. The fluid volume change may be calculated after the occurrence of a fluid distribution into a body segment. In one embodiment, the occurrence of fluid redistribution may occur during a cardiac cycle. The determination of fluid-volume change in a body segment may be used to measure the fluid flow in a body segment by multiplying the fluid-volume change amount by the heart rate of a patient.

An alternative embodiment to FIG. 3 further comprises acquiring an electrocardiogram (block 308). The electrocardiogram of block 308 may be used for R-wave detection between RR intervals to synchronize signal processing and calculation of a heart rate. Determining a heart rate may be useful in measuring the fluid flow in a body segment.

Exemplary Implementations

Various examples of computer systems and methods for embodiments of the present disclosure have been described above. Listed and explained below are alternative embodiments, which may be utilized to measure fluid in a body segment. Specifically, an example embodiment of calculating a fluid change volume in at least one body segment is explained in the description of FIG. 4 below.

Figure 4:
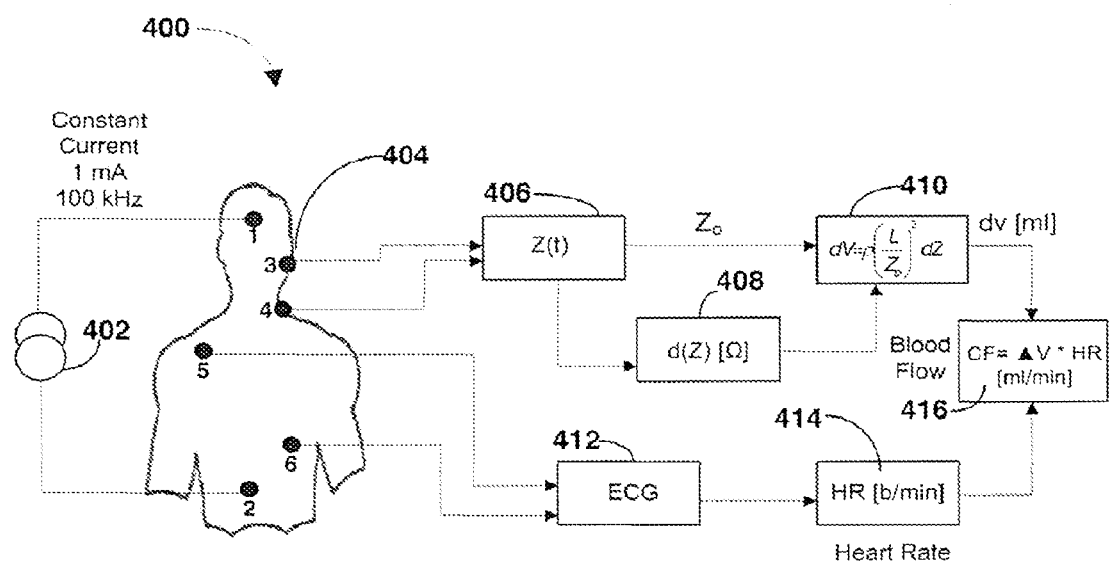
FIG. 4 is a diagram illustrating exemplary measurement principles to measure fluid flow in a body segment, according to an example embodiment.

FIG. 4 is system illustrating exemplary measurement principles to measure fluid flow in a body segment, according to an example embodiment. The system 400 represents one embodiment of a fluid measurement system such as the fluid measurement system 100 described in FIGS. 1 and 6, respectively. Further, the system 400 of FIG. 4 comprises a constant current 402 running through a body segment, a plurality of electrodes 404 attached to the body segment, and a plurality of calculations 406-414 used to determine patient vital signs. Patient vital signs may physiological statistic taken to assess basic bodily functions. A patient may be any living being including humans and animals. In an exemplary embodiment, the fluid in the body segment may be blood. The related patient vital signs measured may include rate of blood flow and heart rate.

A constant current 402 runs through a body segment of a patient. The constant current 402 may be generated by an electrical energy source. An electrical energy source may be any device or apparatus capable of generating an electric current. An example embodiment of an electrical energy source may be a current generator circuit. In one embodiment, the constant current 402 may be a constant sinusoidal alternating current of one (1) mA and one hundred (100) kHz.

The constant current 402 may pass through a plurality of electrodes 404 attached to at least one body segment. In an example embodiment, the constant current 402 may pass longitudinally though the plurality of electrodes 404. In one embodiment, some of the plurality of electrodes 404 may be directly connected to the electrical energy source. In an alternative embodiment, each of the plurality of electrodes 404 may be connected to the electrical source. The plurality of electrodes 404 may be comprised of multiple sets of electrodes attached to various body segments. In an exemplary embodiment, the plurality of electrodes 404 may have three sets of electrodes. A first set of electrodes may be current electrodes. Current electrodes may be directly connected to the electrical source and used to measure the constant current 402. A second set of electrodes, voltage electrodes, may be used to measure the voltage drop between the voltage electrodes placed on various body segments. In one embodiment, the voltage electrodes may be placed on the neck and head of a patient to gain electrical impedance readings in the neck and carotid artery of a patient. A third set of electrodes, electrocardiogram ("ECG") electrodes, may be used to produce an electrocardiographic reading of the patient. The ECG reading may be useful in evaluating cardiovascular activity of the heart over a period of time including determining a heart rate.

A plurality of calculations 406-414 may be used to determine patient vital signs. As previously described, patient vital signs may include evaluating blood flow to a body segment. One exemplary embodiment of a body segment could be a brain. The system 400 may be used to determine blood flow to the brain. The plurality of calculations 406-414 may include applying the Nyboer formula to calculate fluid volume change of a body segment. Assuming that you have two body segments with different cross-sections, the following formula may be applied:

$$dV = \rho L^2 / Z_0^2 \, dZ$$

$$dV = \rho L^2 / Z_0^2 \, dZ$$

where:
dV=volume change of blood [ml]
$p_b$=specific resistance of blood [Ωcm]
L=distance between the measurement electrodes [cm]
$Z_0$=basic impedance between the measurement electrodes [Ω]
dZ=impedance change during blood flow through the artery carotid In measuring blood flow to the brain, the Nyboer formula may be applied to the neck and carotid artery, assuming that the neck and carotid artery form two paraxial cylinders with different cross-sections.

At block 406, the electrical impedance reading of the voltage electrodes may be determined. At block 408, the impedance change during blood flow through the carotid artery is calculated. Both the electrical impedance reading of the voltage electrodes and the impedance change during blood flow through the carotid artery may be used in the Nyboer calculation at block 410. The resulting calculation from block 410 produces the change in fluid volume (in milliliters "mL") of a body segment. In an exemplary embodiment, this value may be used to calculate the blood flow to a body segment such as the brain.

The ECG electrodes may be read at block 412. A heart rate may be determined from the ECG reading at block 414. A blood flow calculation 416 representing blood flow to a body segment can be determined by taking the change in fluid volume of the body segment and multiplying that value by the heart rate of the patient.

Exemplary Hardware and Operating Environment

This section provides an overview of one example of hardware and an operating environment in conjunction with which embodiments of the present disclosure may be implemented. In this exemplary implementation, a software program may be launched from a non-transitory computer-readable medium in a computer-based system to execute functions defined in the software program. Various programming languages may be employed to create software programs designed to implement and perform the methods disclosed herein. The programs may be structured in an object-orientated format using an object-oriented language such as Java or C++. Alternatively, the programs may be structured in a procedure-orientated format using a procedural language, such as assembly or C. The software components may communicate using a number of mechanisms well known to those skilled in the art, such as application program interfaces or inter-process communication techniques, including remote procedure calls. The teachings of various embodiments are not limited to any particular programming language or environment. Thus, other embodiments may be realized, as discussed regarding FIGS. 5 and 6 below.

Figure 5:
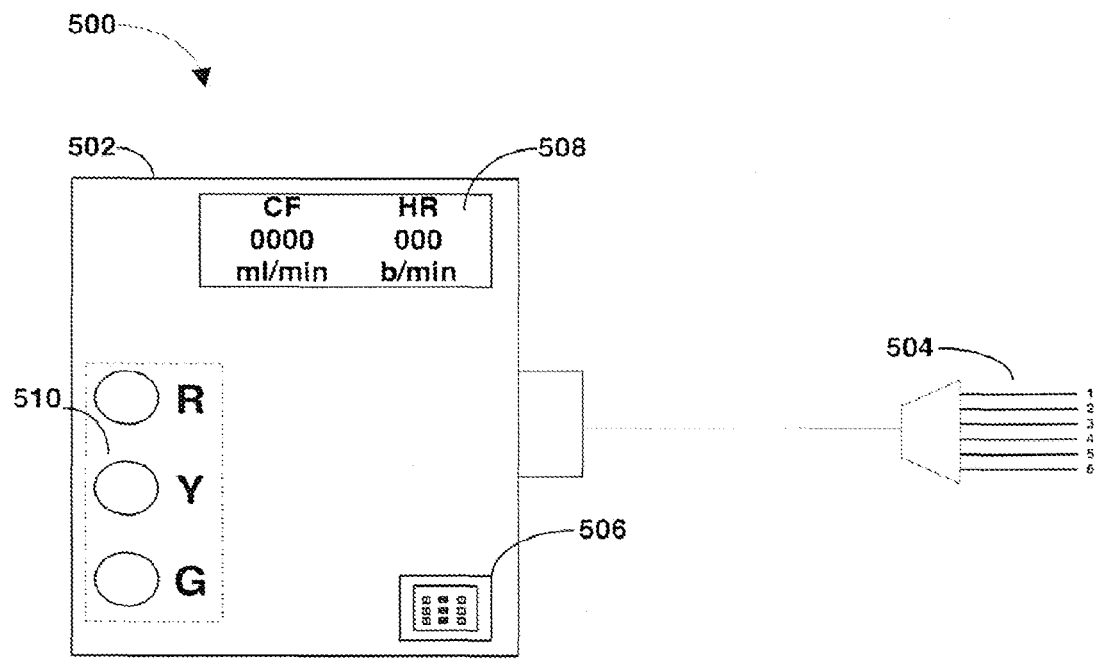
FIG. 5 is a perspective view of an apparatus to measure blood flow, according to an example embodiment.

FIG. 5 is a perspective view of an apparatus to measure blood flow, according to an example embodiment. The apparatus 500 comprises a current generator circuit 502 having a plurality of channels, a plurality of electrodes 504 connected to the current generator circuit 502, a processor 506 attached to the current generator circuit 502, and a display unit 508 connected to the processor 506. The apparatus may be used to measure blood flow to a body segment in a continuous and non-invasive manner.

The current generator circuit 502 may be used to provide a constant and sinusoidal current to the apparatus 500. In one embodiment, a constant and sinusoidal alternating current of 1 mA and 100 kHz may be passed through the apparatus 500. Additionally, the current generator circuit 502 may have a plurality of channels. The plurality of channels may communicate with each other to relay information. In an example embodiment, the plurality of channels may include an electrical impedance channel. The electrical impedance channel may allow for a number of electrical impedance readings to be detected and registered by the plurality of electrodes 504 and used in the plurality of calculations performed on the processor 506. In another example embodiment, the current generator circuit 502 may have an ECG channel. The ECG channel may be used to provide an ECG signal and detect the RR interval, which may be used to calculate heart rate, and also in a calculation to determine blood flow of at least one body segment.

A plurality of electrodes 504 may be connected to the current generator circuit 502. The plurality of electrodes 504 may also be attached to at least one body segment of a patient. A patient may be any living being for which vital signs may be detected, including humans and animals. The plurality of electrodes 504 may be used to determine a plurality of electrical impedance readings by applying a four-electrode method to the plurality of electrodes. In the example 4-electrode method, a constant sinusoidal alternating current is passed longitudinally through a first set of electrodes (one (1) and two (2)). A voltage drop is measured between a second set of electrodes (three (3) and four (4)). In an exemplary embodiment, the plurality of electrodes 504 may have more than four electrodes connected to body segments of the patient including ECG electrodes to measure an ECG signal used to evaluate a heart rate of a patient.

Electrical impedance measures the opposition to alternating current in a circuit. Measuring electrical impedance may capture relative amplitude, voltages and related phases of the current. Applying a constant current through a body segment may allow the plurality of electrodes 504 to capture the changes in flow of the electrical current as the fluid-volume content changes. The plurality of electrical impedance readings may include a blood flow reading and a heart rate reading. An original electrical impedance reading may be detected by connecting the plurality of electrodes 504 to a body segment. As the fluid-volume content changes in a body segment, derivative impedance may be detected. Both the original electrical impedance reading and the derivative electrical impedance reading may be used in the calculation of blood flow to a body segment.

A processor 506 may be attached to the current generator circuit 502 to compute a plurality of calculations. The plurality of calculations may include applying a Nyboer formula to the plurality of electrical impedance readings to determine blood flow in a body segment. Please refer to the "example implementations" section of the detailed description for a breakdown of the Nyboer formula. Other calculations related to patient vital signs may also be included in the plurality of calculations.

A display unit 508 may be connected to the processor 506. The display unit 508 may be used to display numeric values of both the plurality of electrical impedance readings and the plurality of calculations. Both of these readings may be used to indicate the patient's vital signs. Patient vital signs detected may include blood flow and heart rate. In one example embodiment, the display unit 508 may numerically illustrate the patient's heart rate and also the calculated blood flow to a body segment. In another embodiment, the display unit 508 may illustrate more complex graphical and pictorial representations of the patient's vital signs. The processor 506 may generate such representations.

An alternative embodiment of the apparatus 500 to measure blood flow may further comprise a plurality of indicators 510 connected to the processor 506. The plurality of indicators 510 may be used to indicate a health status of a patient. A patient's health status may be determined from the combination of the results of the plurality of electrical impedance readings and the plurality of calculations. In one example embodiment, the plurality of indicators 510 may be color-coded lights to visibly alert a health professional of the health status of the patient. In one embodiment, the plurality of indicator 510 lights may be light-emitting diodes ("LEDs"). For example, a red LED may be used to indicate that the condition of a patient's health status is dangerous and attention is needed. A yellow LED may be used to indicate that the patient's health status is heading towards a dangerous condition and should be monitored. A green LED light may be used to indicate that the patient's health status is safe. In another embodiment, the plurality of indicators 510 may be auditory.

FIG. 6 is a block diagram illustrating a fluid measurement system, according to an example embodiment. Such embodiments may comprise a computer, a memory system, a magnetic or optical disk, some other storage device, or any type of electronic device or system. The computer system 600 may include one or more processor(s) 602 coupled to a non-transitory machine-accessible medium such as memory 604 (e.g., a memory including electrical, optical, or electromagnetic elements). The medium may contain associated information 606 (e.g. computer program instructions, data, or both) which when accessed, results in a machine (e.g. the processor(s) 602) performing the activities previously described herein.

CONCLUSION

This has been a detailed description of some exemplary embodiments of the present disclosure contained within the disclosed subject matter. The detailed description refers to the accompanying drawings that form a part hereof and which show by way of illustration, but not of limitation, some specific embodiments of the present disclosure, including a preferred embodiment. These embodiments are described in sufficient detail to enable those of ordinary skill in the art to understand and implement the present disclosure. Other embodiments may be utilized and changes may be made without departing from the scope of the present disclosure. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, the present disclosure lies in less than all features of a single disclosed embodiment. Thus, the following claims are hereby incorporated into the Detailed Description, with each claim standing on its own as a separate preferred embodiment. It will be readily understood to those skilled in the art that various other changes in the details, material, and arrangements of the parts and method stages which have been described and illustrated in order to explain the nature of this disclosure may be made without departing from the principles and scope as expressed in the subjoined claims.

It is emphasized that the Abstract is provided to comply with requirements for an Abstract that will allow the reader to quickly ascertain the nature and gist of the technical disclosure. It is submitted with the understanding that it will not be used to interpret or limit the scope or meaning of the claims.

The invention claimed is:

1. A computer system to measure fluid in a human body segment comprising:
    a current generation module emitting an electrical current through at least one body segment to measure a fluid-volume content of the at least one body segment;
    an electrode module having a plurality of electrodes attached to the at least one body segment; and wherein said plurality of electrodes have three sets of electrodes including a first set of current electrodes directly connected to the current generation module and used to measure the constant current, a second set of voltage electrodes used to measure the voltage drop between the voltage electrodes placed on the neck and head of a patient to gain electrical impedance readings in the neck and carotid artery of the patient and a third set of electrocardiogram electrodes to produce an electrocardiograph reading of the patient;
    a signal-processing module to measure changes in flow of the electrical current through the at least one body segment as the fluid-volume of the at least one body segment changes; and
    an impedance calculation module to calculate a fluid flow through the at least one body segment by determining a fluid-volume change in the at least one body segment and applying a Nyboer formula; and,
    wherein a constant sinusoidal alternating current is emitted through a first set of electrodes with a current of one (1) milliampere ("mA") and one hundred (100) kilohertz ("kHz") that pass longitudinally through said first set of electrodes and as attached to at least one of said body segments; and,
    further comprising a display module to illustrate a representation of the electrical current through the at least one body segment; and
    an electrocardiogram module using an electrocardiogram signal for R-wave detection to synchronize signal processing and calculation of a heart rate; and
    wherein the signal-processing module uses a four-electrode method to determine impedance change of the electric current through the at least one body segment.

2. The computer system of claim 1, wherein the current generation module further comprises a current generator circuit used to generate a constant sinusoidal alternating current.

* * * * *